US007428048B1

(12) United States Patent  
Farkas et al.

(10) Patent No.: US 7,428,048 B1
(45) Date of Patent: Sep. 23, 2008

(54) IMAGING ELASTIC SCATTERING SPECTROSCOPY

(75) Inventors: Daniel L. Farkas, Los Angeles, CA (US); Elliot S. Wachman, Lakewood, NJ (US); Jill Wachman, Lakewood, NJ (US); Miriam Farkas, Los Angeles, CA (US); Erik H. Lindsley, Los Angeles, CA (US)

(73) Assignee: Spectral Molecular Imaging Inc., Los Angeles, CA (US)

( * ) Notice: Subject to any disclaimer, the term of this patent is extended or adjusted under 35 U.S.C. 154(b) by 203 days.

(21) Appl. No.: 11/026,912

(22) Filed: Dec. 30, 2004

(51) Int. Cl.
*G01J 4/00* (2006.01)
(52) U.S. Cl. ..................................... 356/364
(58) Field of Classification Search ................. 356/364
See application file for complete search history.

(56) References Cited

U.S. PATENT DOCUMENTS

| | | | | |
|---|---|---|---|---|
| 4,271,829 A * | 6/1981 | Heckele | ...................... | 600/117 |
| 4,980,763 A * | 12/1990 | Lia | .............................. | 348/67 |
| 5,111,038 A * | 5/1992 | Taylor et al. | ................ | 250/225 |
| 5,214,538 A * | 5/1993 | Lobb | .......................... | 359/691 |
| 5,303,026 A | 4/1994 | Strobl et al. | | |
| 5,318,024 A | 6/1994 | Kittrell et al. | | |
| 5,477,321 A * | 12/1995 | Johnson | ...................... | 356/319 |
| 5,545,120 A * | 8/1996 | Chen et al. | .................. | 600/117 |
| 5,693,003 A * | 12/1997 | Wolfelschneider et al. | .. | 600/117 |
| 5,769,791 A | 6/1998 | Benaron et al. | | |
| 5,785,658 A | 7/1998 | Benaron et al. | | |
| 5,807,261 A | 9/1998 | Benaron et al. | | |
| 6,011,626 A * | 1/2000 | Hielscher et al. | ............ | 356/367 |
| 6,091,983 A * | 7/2000 | Alfano et al. | ............... | 600/431 |
| 6,091,984 A | 7/2000 | Perelman et al. | | |
| 6,177,984 B1 * | 1/2001 | Jacques | ....................... | 356/39 |
| 6,373,568 B1 | 4/2002 | Miller et al. | | |
| 6,381,018 B1 | 4/2002 | Bigio et al. | | |
| 6,404,497 B1 * | 6/2002 | Backman et al. | ............ | 356/369 |
| 6,437,856 B1 * | 8/2002 | Jacques | ....................... | 356/39 |
| 6,482,148 B1 * | 11/2002 | Luke | .......................... | 600/117 |
| 6,519,032 B1 | 2/2003 | Kuebler et al. | | |
| 6,529,769 B2 | 3/2003 | Zigler | | |

(Continued)

OTHER PUBLICATIONS

Principles of Optics, Born and Wolf, seventh edition, 1999, section 14. 5 Diffraction by a conducting sphere; theory of Mie.*

(Continued)

*Primary Examiner*—Patrick J Connolly
*Assistant Examiner*—Jonathan Skovholt
(74) *Attorney, Agent, or Firm*—Fish & Richardson P.C.

(57) ABSTRACT

An apparatus for image elastic scattering spectroscopy is disclosed that is comprised of a light source for generating polarized light. Means are provided to convey the polarized light to a target. A collector receives light reflected from the target. A detector is responsive to the collector for generating images at both parallel and perpendicular polarizations for each of a plurality of wavelengths. A range finder detects a distance to the target. Control electronics control the image generation and the range finder. The apparatus may be configured to image areas on the surface of the body or configured so as to be inserted into various body cavities. Typically, the apparatus will be used in conjunction with an analyzer for analyzing the images for evidence of abnormal cells. Methods of gathering data and of screening for abnormal cells are also disclosed.

22 Claims, 6 Drawing Sheets

U.S. PATENT DOCUMENTS

| | | | |
|---|---|---|---|
| 6,567,678 B1 * | 5/2003 | Oosta et al. | 600/316 |
| 6,615,064 B1 * | 9/2003 | Aldrich | 600/316 |
| 6,624,889 B1 * | 9/2003 | Li | 356/365 |
| 6,639,674 B2 * | 10/2003 | Sokolov et al. | 356/369 |
| 6,704,105 B1 * | 3/2004 | Swanson et al. | 356/336 |
| 7,103,402 B2 * | 9/2006 | Vo-Dinh | 600/476 |
| 2002/0002080 A1 | 1/2002 | Stockdale | |
| 2002/0101593 A1 | 8/2002 | Yang et al. | |
| 2002/0135752 A1 | 9/2002 | Sokolov et al. | |
| 2002/0143243 A1 | 10/2002 | Georgakoudi et al. | |
| 2002/0165456 A1 | 11/2002 | Canpolat et al. | |
| 2002/0171831 A1 * | 11/2002 | Backman et al. | 356/369 |
| 2002/0177777 A1 | 11/2002 | Nordstrom et al. | |
| 2003/0013973 A1 | 1/2003 | Georgakoudi et al. | |
| 2005/0128482 A1 * | 6/2005 | Gibbs | 356/364 |
| 2005/0240077 A1 * | 10/2005 | Rovegno | 600/108 |
| 2005/0264813 A1 * | 12/2005 | Giakos | 356/369 |
| 2006/0001876 A1 * | 1/2006 | Gibbs et al. | 356/364 |

OTHER PUBLICATIONS

Elliot S. Wachman et al., "Imaging acousto-optic tunable filter with 0.35-micrometer spatial resolution", *Applied Optics*, vol. 35, No. 25, pp. 5220-5226 (Sep. 1, 1996).

Erik Herbert Lindsley, "Endoscopic Imaging Elastic Scattering Spectroscopy for In Vivo Detection of Lung Cancer", *Thesis submitted to the Graduate Faculty of the School of Engineering of the University of Pittsburgh,*, pp. ii-141 (dated 2005).

Lev T. Perelman et al, "Light Scattering Spectroscopy of Epithelial Tissues: Principles and Applications", *Handbook of Optical Biomedical Diagnostics*, ISBN-10: 0819442380 (Jun. 2002).

* cited by examiner

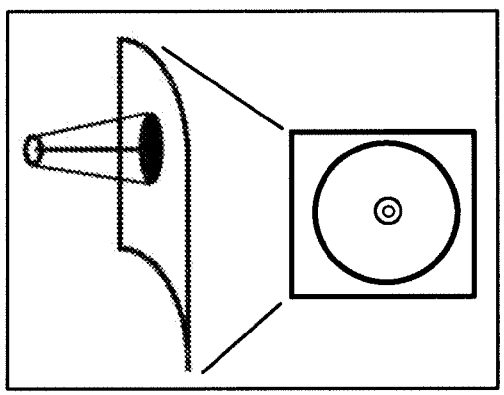 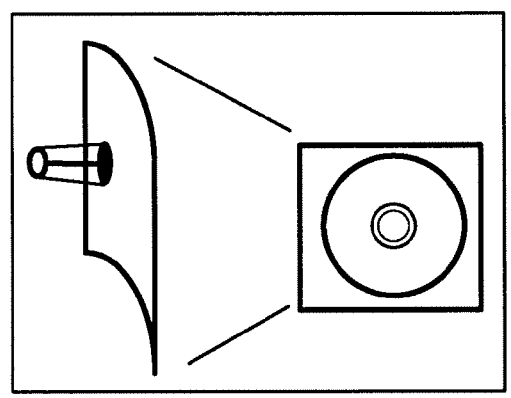
FIG. 5BFIG. 5C

IMAGING ELASTIC SCATTERING SPECTROSCOPY

BACKGROUND OF THE INVENTION

1. Field of the Invention

The present invention is broadly concerned with providing a non-invasive technique for the early detection of cancer and other abnormal tissue and, more particularly, to the field of imaging elastic scattering spectroscopy (IESS).

2. Description of the Background

Detecting abnormal tissue early is critical to the successful treatment of disease. Life expectancy of patients with malignancy or cancer, for example, can increase dramatically when abnormal tissue is identified while still in a pre-malignant state. Such tissue regions, dysplasia and carcinoma in situ being typical examples, are ordinarily detected by surgical biopsy. The removed tissue is sent to a pathologist, where it is examined under a microscope for the characteristic morphological changes that indicate abnormal cell growth. Upon receiving the pathology report, the physician can then decide whether further removal of the tissue is indicated.

This method of treatment has a number of serious drawbacks. For example, only a limited number of regions can be biopsied, with the choice of region determined only by its gross appearance in the eyes of the physician. It is therefore quite likely that a problem area, particularly one in an early stage of abnormality, may be missed completely. Another serious drawback of this method of treatment is that since the identification of abnormality must await the pathology report, surgical removal of the abnormal tissue often must be performed during a separate procedure (and sometimes even by successive iterations), thereby increasing risk to the patient, and inconvenience and cost for both the patient and the physician.

Within the last decade or so, a number of all-optical techniques for identifying abnormal tissue have been developed in an attempt to avoid these problems. These approaches have the potential for allowing problem sites to be detected over a large area sensitively and quickly, without having to rely on the subjective judgment of the physician. In addition, because suspicious areas can be identified during the initial examination, diseased tissue can be removed immediately, and completeness of the excision assessed by prompt reimaging of the area in question.

The most developed of these optical techniques makes use of differences in the spectra of fluorescence exhibited by normal and abnormal tissue. This fluorescence is ordinarily excited by laser illumination, and can be either intrinsic or extrinsic. Although numerous groups are working on the development of fluorescence-based systems for cancer diagnosis, to date only one device has reached the commercial market. The LIFE scope, manufactured by Xillix Inc. and marketed by Olympus, Inc., uses ultraviolet laser light to excite tissue autofluorescence through a bronchoscope. It is presently being used by approximately 50 groups worldwide with a cost of upwards of $200,000 per unit. Although this device provides much greater sensitivity than standard white-light bronchoscopy, single procedures can be very time consuming. Even experienced surgeons often require 45 minutes to perform one examination which would take only 3 minutes using standard bronchoscopy equipment. The use of the LIFE scope is not only quite draining for the patient and physician, but also limits greatly the number of patients that can be seen, thereby substantially increasing procedure cost.

Other groups have used Raman signals to identify abnormal tissue, however these signals are extremely weak, and it may be difficult to implement as a practical clinical tool.

A third approach, elastic scattering spectroscopy (ESS), illuminates the sample, and looks at the spectral content of the light scattered from tissue right beneath the surface by using a point probe in contact with the tissue surface. This method has the capability of detecting disorganized epithelial orientation and architecture, morphological changes in epithelial surface texture and thickness, cell crowding, enlargement and hyperchromicity of cell nuclei, increased concentration of metabolic organelles, and the presence of abnormal protein packages. ESS has been used to study the skin, the eyes, the bladder, the prostate and many different regions of the gastrointestinal tract. In one study, ESS was used to differentiate neoplastic from non-neoplastic tissue and adenomatous polyps from hyperplasic polyps in the colon with a predictive accuracy of ~85%. In another study ESS was used to detect bladder cancer with a sensitivity of 100% and a specificity of 97%. Preliminary tests of this technique in the lower GI tract demonstrated the ability of differentiating between dysplasia, adenoma/adenocarcinoma, and normal mucosa with a sensitivity of 100% and a specificity of 98%. Studies in the skin have demonstrated a sensitivity of 90.3% and a specificity of 77.4% for distinguishing primary melanomas from benign nevi. Over a decade of clinical trials with this instrument in a variety of organ systems has shown that these spectra can provide a sensitivity means of detecting even early abnormal tissue. At present, however, this method is capable of providing single point measurements only, thereby making it inappropriate for routine clinical use.

Therefore, there is a need in the art for a system for detecting ESS signals in a full imaging mode which can be equally applicable to imaging endoscopically and imaging externally for routine clinical use.

SUMMARY OF THE PRESENT INVENTION

One aspect of the present invention is a method of generating data which comprises illuminating a target with polarized light and serially imaging the target at both parallel and perpendicular polarizations for each of a plurality of different wavelengths. The serially imaging may include: illuminating the target with a wavelength-tunable light source; illuminating the target with a broadband light source in series with a wavelength-tunable filter; illuminating the target with a broadband light source and detecting reflected light with a wavelength-tunable detector, including, for example, a detector whose wavelength acceptance can be chosen by interposing chromatic filters in the light path; or illuminating the target with a broadband light source and detecting reflected light with a wavelength-tunable filter in series with a detector.

Another aspect of the present invention is a method of generating data which comprises illuminating a target with polarized light, serially imaging the target at both parallel and perpendicular polarizations for each of a plurality of different wavelengths and determining range information indicative of a distance to the target. Again, the serially imaging may include: illuminating the target with a wavelength-tunable light source; illuminating the target with a broadband light source in series with a wavelength-tunable filter; illuminating the target with a broadband light source and detecting reflected light with a wavelength-tunable detector, including, for example, a detector whose wavelength acceptance can be chosen by interposing chromatic filters in the light path or illuminating the target with a broadband light source and detecting reflected light with a wavelength-tunable filter in series with a detector. Additionally, determining range information may be accomplished optically, sonically and/or mechanically. Further, determining range information may be accomplished by illuminating a spot of the target with a collimated beam of known diameter and degree of collimation, recording the size of the illuminated spot reflected from the target, and calculating the distance to the target using the size of the illuminated spot and the known diameter and degree of collimation of the beam.

Another aspect of the present invention is screening for abnormal cells and is comprised of illuminating a target with polarized light, serially producing a series of images of the target at both parallel and perpendicular polarizations for each of a plurality of different wavelengths, determining a distance to the target, and analyzing the series of images based on the distance to identify abnormal cells. The analysis may include an analysis based on Mie theory mathematics.

The present invention is also directed to an apparatus comprising a light source for generating polarized light. Means are provided to convey the polarized light to a target. A collector receives light reflected from the target. A detector is responsive to the collector for generating images at both parallel and perpendicular polarizations for each of a plurality of wavelengths. A range finder detects a distance to the target. The apparatus is under the control of control electronics and may be configured to image areas on the surface of the body, or configured so as to be inserted into various body cavities. Typically, the apparatus would be used in conjunction with an analyzer for analyzing the images for evidence of abnormal cells.

To enable the generation of images at a plurality of wavelengths, either the source of light or the detector is wavelength tunable. The polarizers may include any of a variety of known polarizing devices including, but not limited to a polarizing sheet, a polarizing beamsplitter, or a polarizing-preserving fiber. The range finder may be an optical, acoustical and/or mechanical device.

The present invention provides a non-invasive technique for the early detection of cancer and other abnormal tissue. The present invention allows for detecting ESS signals in a full imaging mode which can be equally applicable to imaging endoscopically and imaging externally for routine clinical use.

BRIEF DESCRIPTION OF THE DRAWINGS

To enable the present invention to be easily understood and readily practiced, the present invention will now be described for purposes of illustration and not limitation, in connection with the following figures wherein:

FIGS. 5B and 5C are detailed diagrams illustrating a range finding mechanism useful for determining the distance between the tissue and probe which may be a component of the present invention.

DETAILED DESCRIPTION OF THE INVENTION

Figure 1:
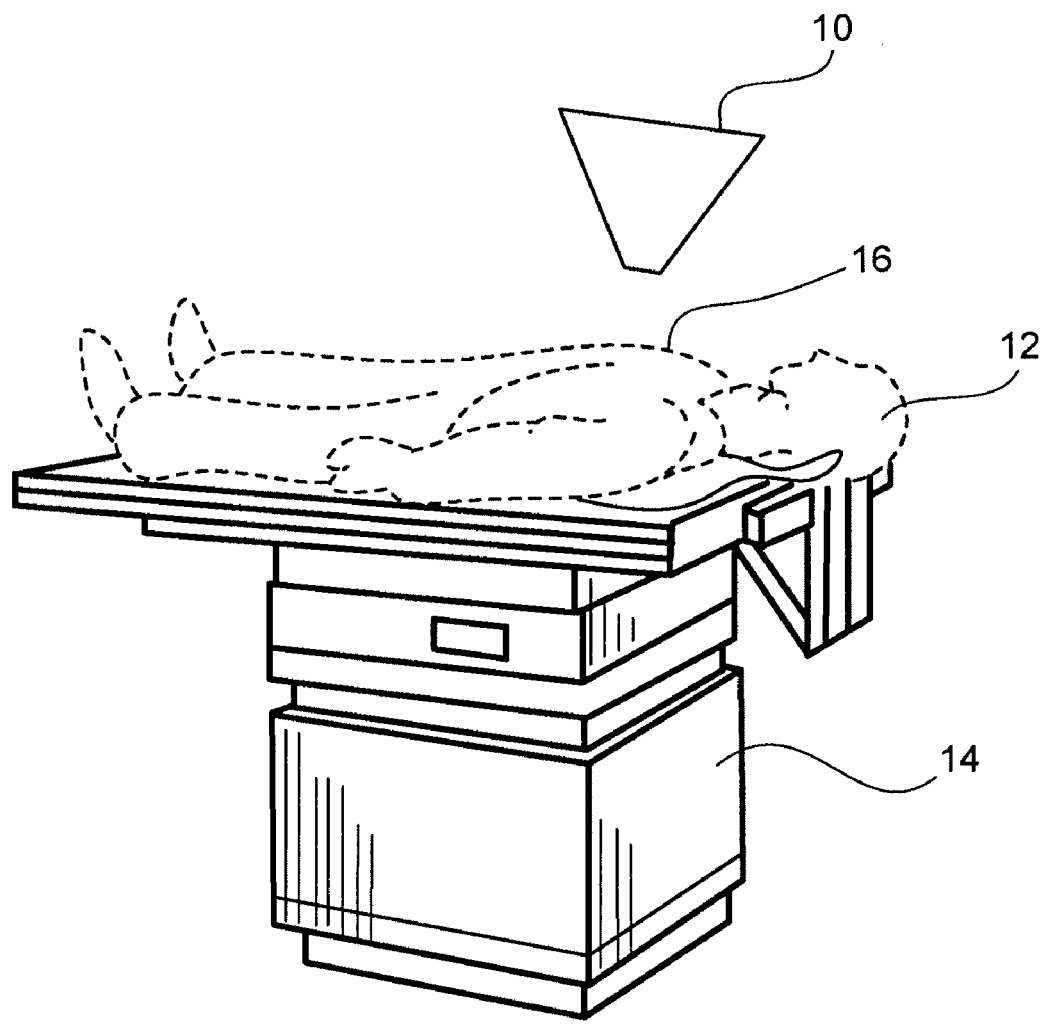
FIG. 1 illustrates an apparatus constructed according to the present invention used in a process for screening for abnormal cells.

One embodiment of an apparatus 10 constructed according to the teachings of the present invention and useful for screening for abnormal cells is illustrated in FIG. 1. In FIG. 1, a patient 12 is positioned on an examining table 14. A target 16 is examined by apparatus 10 as will be described in detail below. Those of ordinary skill in the art will recognize that target 16 is meant to be exemplary and not limiting.

Most internal and external surfaces of the body are covered with a layer of cells known as the epithelium. One of the more common types of epithelial tissue is known as the "columnar epithelium", in which a single layer of epithelial cells lies on top of the thicker sub-mucosal layer. In such a case, the epithelial nuclei can be considered as scattering spheres embedded in a surrounding uniform medium of different optical composition.

The way that light scatters in such a situation depends upon a number of factors: scattering angle, sphere size, wavelength and polarization of the light being scattered, as well as the optical properties of the spheres and surrounding medium. The mathematics used to describe this scattering is known as the Mie theory. Hence, if the wavelengths and polarization of the illumination light, the detection angle, and the optical properties of the tissue are know, the Mie theory can be used to calculate the size of the nuclear spheres responsible for the observed scatter. If a camera is used to produce images of the light reflected from the target 16, then an analysis of the images will result in a map of nuclear size at each point in the tissue imaged. This is the basis of imaging elastic scattering spectroscopy (IESS).

Figure 2:
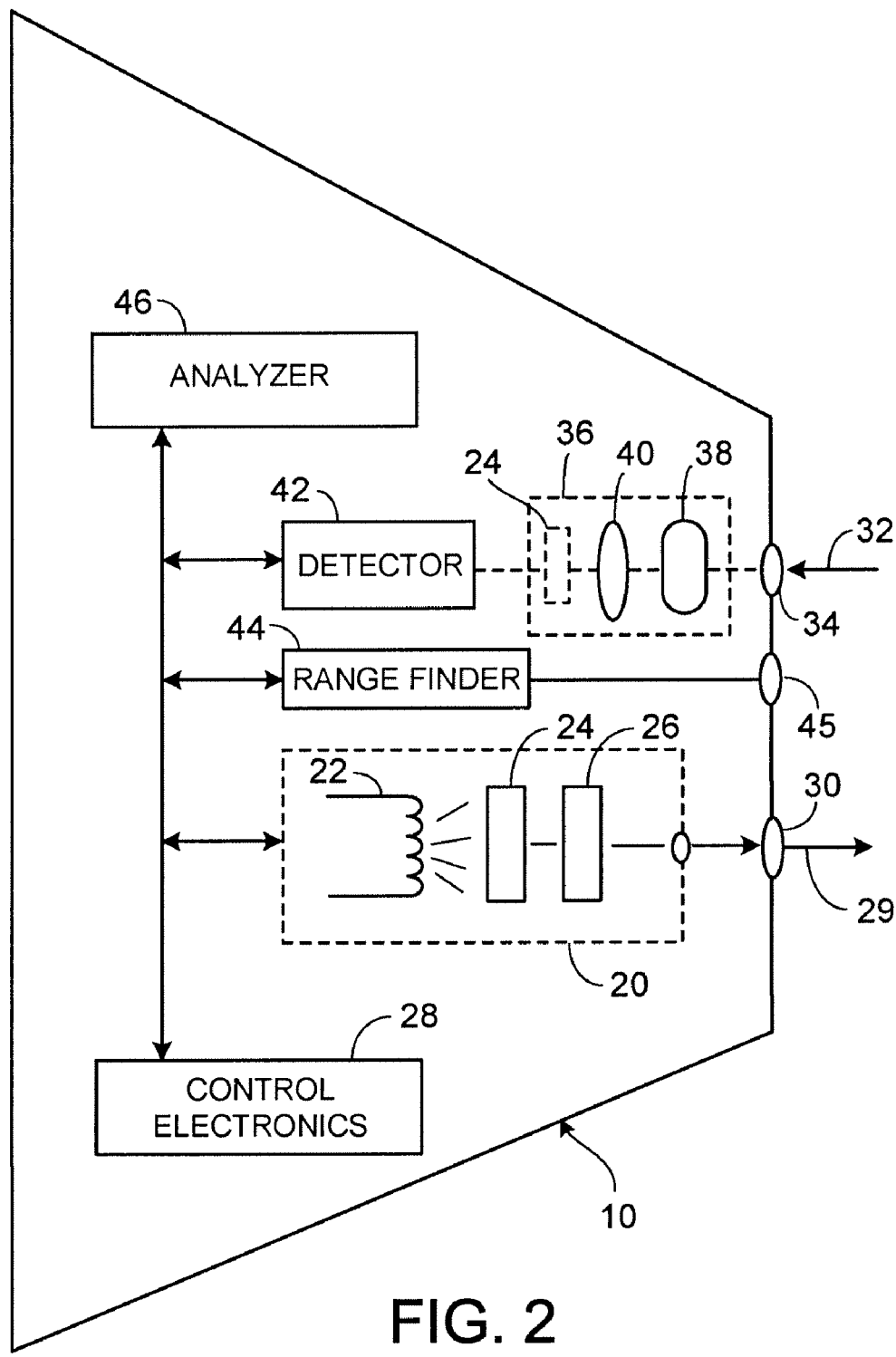
FIG. 2 is a block diagram of one embodiment of the apparatus shown in FIG. 1.

The apparatus 10 shown if FIG. 1 is illustrated in greater detail in FIG. 2. In FIG. 2, a light source 20 is used to generate polarized light. The light source 20 may be comprised of a filament 22 or other source of light. Filament 22 may be a tunable light source or a broadband light source. Should filament 22 be a tunable light source, it is preferably capable of rapidly switching between wavelengths. Should filament 22 be a broadband light source, a tunable filter 24 may optionally be used in series with filament 22 to provide light at discrete wavelengths. Tunable filter 24 should be a device that is capable of rapidly switching between wavelengths, such as an acousto-optic tunable filter (AOTF) or monochromator. The light 29 from light source 20 exists device 10 through an illumination port 30 for illuminating the target 16. The light source 20 is directly in line with illumination port 30, or fiber optics may be used to convey light to the illumination port 30. Additionally, a polarizer 26 may be included in light source 20 within the light path to polarize the light. Polarizer 26 could be any device that polarizes light, for example, a polarizing sheet, a polarizing beamsplitter, a polarizing-preserving fiber, among others. Those of ordinary skill in the art will recognize that polarizer 26 may be any polarizing element known in the art. The light source is under the control of control electronics 28.

Target 16 may be any tissue, including external tissue, such as the skin, or internal tissue such as those accessible endoscopically or otherwise, as will be described below. The light 29 is polarized at this point and may be serially tuned through a plurality of wavelengths by the filter 24. Alternatively, and as will become apparent, the light could remain broadband, with the tuning occurring on the detection side of apparatus 10.

Light 32 reflected from target 16 is received by an imaging port 34. A collector, or series of collection components, 36 is responsive to the light 32 collected at the imaging port 34. Collection components 36 may include polarization filters 38 and imaging optics 40. An imaging detector 42 is responsive to the collector 36 for generating images at both parallel and perpendicular polarizations for each of a plurality of wavelengths. If filament 22 is a broadband light source, and light source 20 does not include tunable filter 24, collection components 36 may contain a tunable filter 24 to provide for spectral discrimination. Tunable filter 24 should be a device that is capable of rapidly switching between wavelengths, such as an acousto-optic tunable filter (AOTF) or monocromator. The imaging detector 42 is under the control of control electronics 28 and, when collector 36 contains a tunable filter, the collector 36 will also be under the control of control electronics 28.

Apparatus 10 includes a range finder 44 for detecting the distance between a range finding port 45 and target 16. Ranger finder 44 may be implemented using any known form of optical, acoustical (sonic) or mechanical range finding device. Range finder 44 is under the control of control electronics 28 and will produce range information for each target 16.

An analyzer 46, which may be integral with apparatus 10 or remote from apparatus 10, is responsive to the images and the range information. Based on the range information, the images are analyzed to identify abnormal cells using the aforementioned Mie theory.

Figure 3:
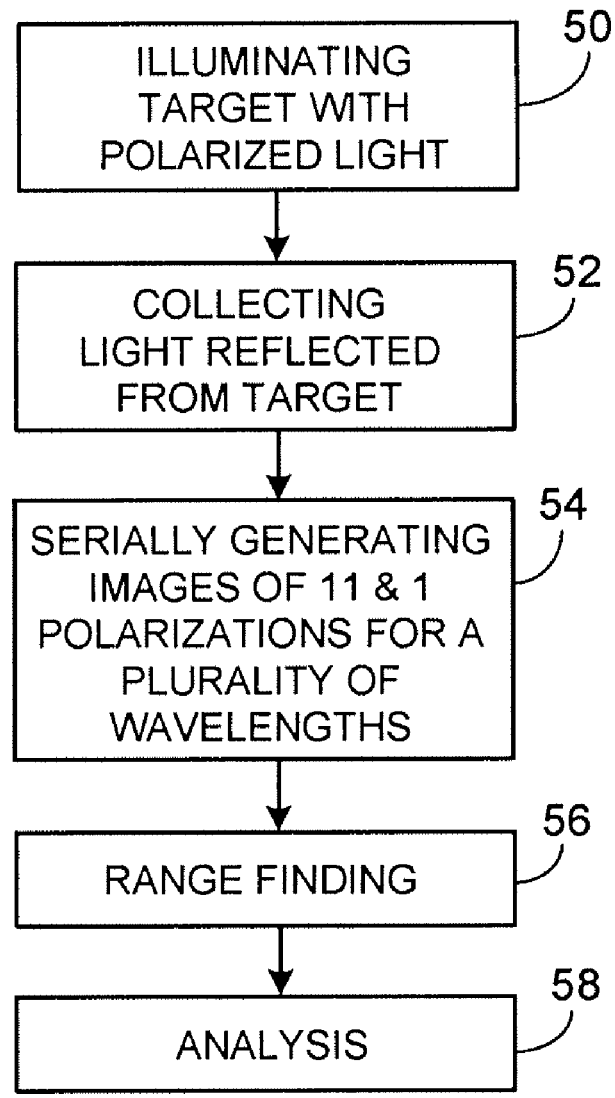
FIG. 3 is a diagram illustrating the steps of a method of screening according to the present invention.

A method of operating the apparatus 10 of the present invention is illustrated in FIG. 3. In FIG. 3, at step 50, polarized light 29 is used to illuminate target 16. At step 52, light reflected from the target is collected. At step 54 the collected light is used to serially create images at both parallel and perpendicular polarizations at a plurality of wavelengths. The resulting set of images provides elastic scattering spectra at each imaged point.

Step 50 may include illuminating the target with a tunable light source or a broadband light source in series with a tunable filter. Alternatively, step 50 may include illuminating the target with a broadband light source and step 54 may include detecting reflected light with a tunable detector or with a tunable filter in series with a detector.

At step 56 range information indicative of the distance to the target, e.g. the distance between the target and the range finding port 45, is generated. The range information may be generated optically, sonically, or mechanically. Although FIG. 3 illustrates the range finding step after steps 50, 52 and 54, the range finding operation can be performed either before or in parallel with steps 50, 52 and/or 54.

Steps 50, 52 and 54 may be referred to as a method of generating data as those steps result in the production of the images needed to screen for abnormal cells. The method of generating data may also include the range finding operation represented by step 56.

At step 58 the generated images are analyzed based on the distance information. This analysis may include an analysis based on the Mie theory. The analysis may determine the nuclear size distribution point-by-point throughout the imaged region. Because size information is a parameter often used by a pathologist when diagnosing biopsied tissue, the analysis results may optionally be pictorially displayed before the physician (with, for example, different sizes depicted in false color), thereby providing a near real-time assessment of the nature of the tissue being examined. Those of ordinary skill in the art will recognize that the screening for abnormal cells can be done offline. That is, steps 50, 52, 54 and 56 may be performed and the data transmitted to a remote location for analysis or stored for later analysis.

Figure 4:
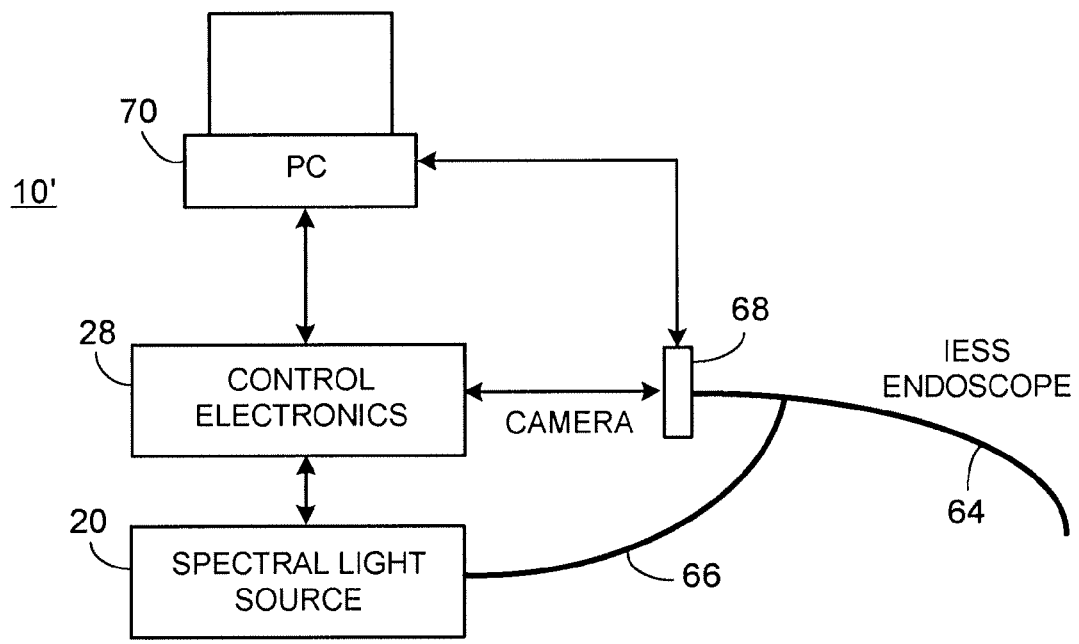
FIG. 4 is a diagram of another embodiment of the present invention useful for screening for abnormal cells in a body cavity.

FIG. 4 illustrates another embodiment of the present invention in which the apparatus 10' is configured for screening for abnormal cells in a body cavity. A portion of the apparatus 10' may be designed as an imaging probe to be inserted into and removed from an instrument channel of a conventional endoscope 64, or incorporated as a permanent additional port in a modified endoscope.

As shown FIG. 4, light source 20 may be a spectral light source. Light source 20 may be a monochromator (Polychrome IV, Till Photonics, Eugene, Oreg.) or AOTF-based source (ChromoDynamics, Inc., Lakewood, N.J.), fed through a first optical fiber 66 which leads to the distal end of an endoscope probe. First optical fiber 66 provides a means for conveying the polarized light. In an endoscopic embodiment, fiber optics are the most practical way of conveying the light from the light source. In other embodiments, mirrors, beam splitters, prisms, reflective devices, fiber optics, direct paths and the like may be used as means for conveying. Polarization of the illumination light may be provided by sheet polarizers (not shown) at the two illumination ports 30 (see FIG. 5A) instead of using polarizer 26 as shown in FIG. 2, or by other means. The single imaging port 34 (see FIG. 5A) has a second optical path (which may be provided by a pair of optical fibers or a lens system as shown in FIGS. 6A and 6B) responsive thereto to direct the collected light to the collector 36 discussed in detail with FIGS. 6A and 6B. The optical fiber 66 has an outer diameter and length compatible with insertion down the instrument channel of conventional endoscopes (for many scopes, this necessitates an outer diameter less than 2.0 mm).

Figure 5A:
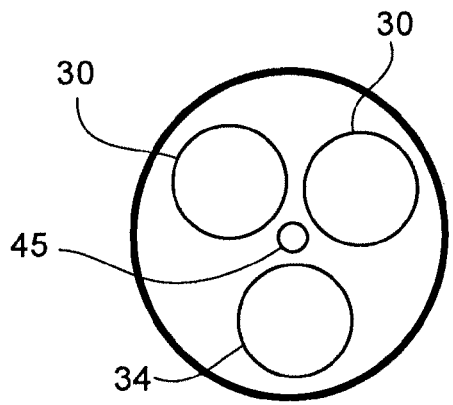
FIG. 5A is a detailed diagram illustrating a port element which may be a component of the present invention.
Figure 6A:
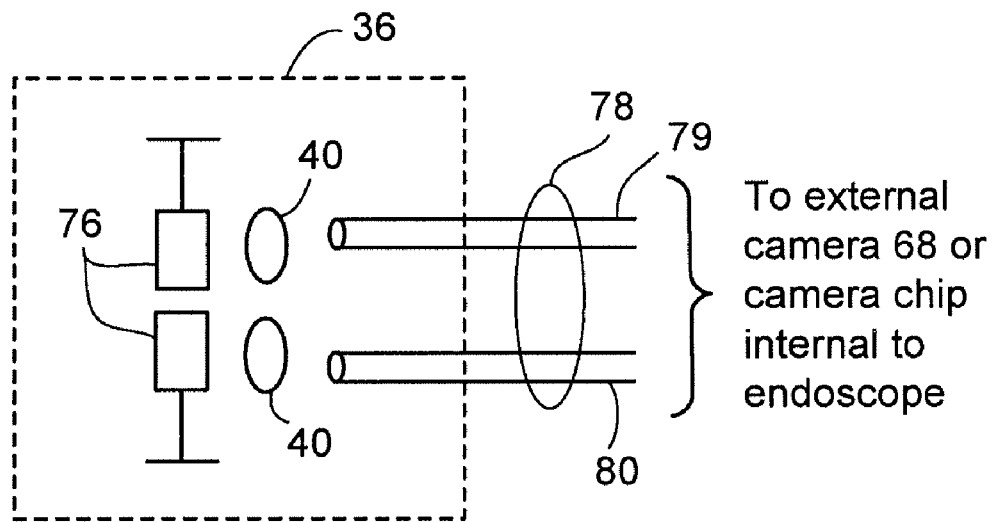
FIGS. 6A and 6B are detailed diagrams illustrating alternative embodiments for the collection components of the present invention.
Figure 6B:
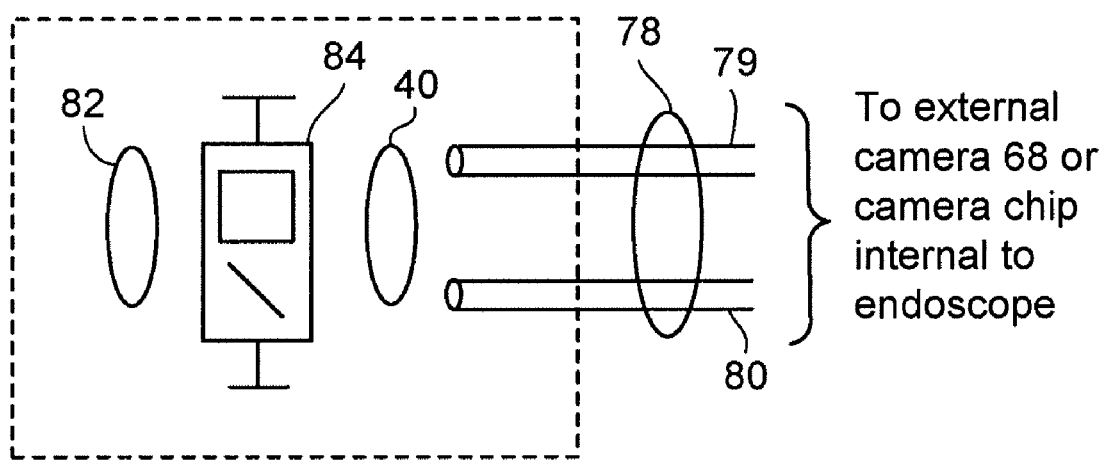

FIG. 5A illustrates range finding port 45. FIGS. 5B and 5C illustrate a simple, inexpensive range finding mechanism useful for determining the distance between the tissue and probe. Range finding may be implemented using a low-power, infrared laser diode fed fiber-optically into an optical range-finding port at the distal end of the endoscope. The output optic on this port will collimate this beam as much as possible to insure that the exiting beam has a very low divergence angle. For a given starting beam diameter and degree of collimation, the size of the spot illuminated on the tissue as a proportion of the entire illuminated field-of-view will vary depending upon the tissue-probe separation, as shown schematically in FIGS. 5B and 5C. At larger separations (as shown in FIG. 5B) the near-collimated range finding laser spot takes up a smaller area of illuminated field of view than at smaller separations (as shown in FIG. 5C). The laser can then be pulsed on once, or several times, per image set, the size of the reflected spot in the tissue measure, and from this, the tissue-probe distance calculated. Although this technique will provide a reasonable determination of distance only in the center of the images field, this should be sufficient for the purposes of the IESS analysis, particularly in regions of fairly regular topology (such as, for example, the esophagus) where tissue-probe distances throughout the imaged area can be readily extrapolated from the value measured at the center of the field. In addition, topology of the illuminated region may also be adduced by looking at the size and shape of the illuminated region.

A camera 68 is affixed to the proximal end of the endoscope 64. The images may be captured with a high-speed black-and-white charged coupled device (CCD) camera (SensiCam VGA, Cooke Corporation, Auburn Hills, Mich.) and sent to a PC computer 70 that performs the function of the analyzer in FIG. 2. PC 70 may contain software and/or hardware for image analysis, classification and display. Camera 68 may be an independent unit proximately mounted to apparatus 64, or an integrated part of apparatus 64, such as an embedded camera chip. Camera 68 is preferably capable of high-speed operation and broad sensitive spectral response for image acquisition.

FIGS. 6A and 6B show examples of other configurations of collection components 36 which may be used. As shown in FIGS. 6A and 6B either polarizing sheets 76 or polarization beam splitting optics 84 can be used to split the parallel and perpendicular polarizations. Collector 36 can include imaging optics 40. Collector 36 may include a portion of optical fibers 79 and 80 or a lens assembly which provide a second optic path 78. The collector 36 may also include collection optics as shown in FIG. 6B. Collector 36 may include a tunable filter 24 such as an AOTF-tunable imaging filter (ChromoDynamics, Inc.).

The fiber optic path provided by the collector 36 may provide a coherent imaging bundle or bundles of optical fibers to deliver images to external camera 68, or to focus the images onto a camera chip (not shown) within endoscope 64. This may also be done by an appropriately designed lens assembly instead of optical fibers. If collection components 36 includes a tunable filter 24 (not shown), tunable filter 24 may be located at any suitable location in the light path.

FIGS. 6A and 6B are intended to illustrate that numerous alternative embodiments of the present invention may be devised by those of ordinary skill in the art. The exact sequence of tuning, polarizing and focusing the light, and whether the tuning is performed on the input side (i.e. prior to the target) or the output side (i.e. after the target) is of no consequence to the present invention. Many components other than those disclosed may be used to perform the desired function, and the selection of one type of component over another may dictate other components that need to be in the light path. Thus, while the present invention has been described in conjunction with presently preferred embodiments, those of ordinary skill in the art will recognize that many modifications and variations are possible. The present invention is intended to be limited only by the scope of the following claims and not by the scope of the disclosed exemplary embodiments.

What is claimed is:

1. An apparatus, comprising:
    a light source for generating polarized light;
    a first fiber optic path having a proximal end optically coupled to said light source and a distal end having an illumination port for illuminating a target;
    a second fiber optic path having a proximal end and a distal end having an imaging port for receiving light emitted from the target in response to the illumination by the illumination port, said first and second fiber optic paths constructed such that said distal ends can be inserted into a body cavity;
    a detector optically coupled to said proximal end of said second fiber optic path for generating images at both parallel and perpendicular polarizations for each of a plurality of wavelengths;
    a range finder for detecting a distance from said distal ends of said fiber optic paths to the target;
    control electronics for controlling the generating of images and the range finder; and
    an analyzer programmed to determine information about the size of scattering elements at different spatial locations of the target based on the generated images and the detected distance.

2. The apparatus of claim 1 wherein either said light source or said detector is wavelength tunable.

3. The apparatus of claim 1 wherein said detector includes a charge coupled device.

4. The apparatus of claim 1 wherein said light source includes a monochromator.

5. The apparatus of claim 1 wherein said light source includes an acousto-optic tunable filter.

6. The apparatus of claim 1 wherein said detector includes an acousto-optic tunable filter.

7. The apparatus of claim 1 wherein said light source includes a polarizing element in series with a source of illumination.

8. The apparatus of claim 1 wherein said range finder includes either an optical, acoustical or mechanical device.

9. The apparatus of claim 1 wherein said range finder comprises:
    a light source for generating a collimated beam of known diameter and degree of collimation for illuminating a spot of said target; and
    a collector for detecting and recording the size of the illuminated spot reflected from said target;
    wherein said control electronics calculates the distance from said distal ends of said fiber optic paths to said target using the size of the illuminated spot and the known diameter and degree of collimation of the beam.

10. A method comprising:
    using an endoscope to illuminate a target with polarized light, the target comprising spatially distributed scattering elements;
    using the endoscope to obtain images of light scattered from the target in response to the illuminating, wherein the scattered light images are obtained for each of a plurality of different wavelengths for each of a first polarization parallel to that for the illumination light and a second polarization perpendicular to that for the illumination light;
    determining range information about a distance to the target from the endoscope;
    analyzing the scattered light images and the range information to determine information about the size of the scattering elements at different spatial locations of the target; and
    outputting the information about the size of the scattering elements.

11. The method of claim 10, wherein using the endoscope to illuminate the target comprises illuminating the target with a wavelength-tunable light source.

12. The method of claim 10, wherein using the endoscope to illuminate the target comprises illuminating the target with a broadband light source in series with a wavelength-tunable filter.

13. The method of claim 12, wherein said wavelength tunable filter is an acousto-optic tunable filter.

14. The method of claim 10, wherein using the endoscope to illuminate the target comprises illuminating the target with a broadband light source and wherein using the endoscope to obtain images comprises detecting reflected light with a detector whose wavelength acceptance can be chosen by interposing chromatic filters in the light path.

15. The method of claim 10, wherein using the endoscope to illuminate the target comprises illuminating the target with a broadband light source and wherein using the endoscope to obtain images comprises detecting reflected/scattered light with a wavelength-tunable filter in series with a detector.

16. The method of claim 15, wherein the wavelength-tunable filter is an acousto-optic tunable filter.

17. The method of claim 10, wherein determining range information comprises either optically, sonically or mechanically determining the range information.

18. The method of claim 10, wherein determining range information comprises:
   illuminating a spot of said target with a collimated beam of known diameter and degree of collimation;
   recording the size of the illuminated spot reflected from said target; and
   calculating the distance to said target using the size of the illuminated spot and the known diameter and degree of collimation of the beam.

19. The method of claim 18, wherein determining range information comprises:
   determining a topology of the illuminated region by analyzing a size and shape of an illuminated region.

20. The method of claim 10, wherein analyzing the scattered light images comprises an analysis based on a Mie theory.

21. The method of claim 10,
   wherein the target comprises epithelial tissue having nuclei corresponding to the scattering elements, and
   wherein the information about the size of the scattering elements at different spatial locations of the target comprises information about the size of the nuclei at different spatial locations of the epithelial tissue, and wherein the method further comprises
   analyzing the information about the size of the nuclei to spatially resolve abnormality of cells of the epithelial tissue.

22. The method of claim 10, wherein the information is outputted as a map of the size of the scattering elements.

* * * * *